US005293993A

United States Patent [19]

Yates, Jr. et al.

[11] Patent Number: 5,293,993

[45] Date of Patent: Mar. 15, 1994

[54] SYRINGE SEALING CONTAINER

[75] Inventors: Marvin P. Yates, Jr., St. Louis, Mo.; Richard C. Cochran, Cypress, Tex.; Ronnie H. Royston, Alexandria, La.

[73] Assignee: Dynamic Bio-Apparatuses, Inc., Houston, Tex.

[21] Appl. No.: 715,365

[22] Filed: Jun. 14, 1991

[51] Int. Cl.[5] .................... B65D 85/20

[52] U.S. Cl. .................... 206/365; 206/470; 206/471

[58] Field of Search .................... 206/363-366, 206/370, 470, 471, 461; 220/339, 359

[56] References Cited

U.S. PATENT DOCUMENTS

| | | | |
|---|---|---|---|
| 3,353,664 | 11/1967 | Armentrout et al. | 206/365 |
| 4,106,621 | 8/1978 | Sorenson | 206/365 |
| 4,921,096 | 5/1990 | McFarlane | 206/363 |
| 4,979,616 | 12/1990 | Clanton | 206/364 |
| 5,031,768 | 7/1991 | Fischer | 206/370 |

*Primary Examiner*—Jimmy G. Foster
*Attorney, Agent, or Firm*—David M. Ostfeld

[57] ABSTRACT

A hypodermic syringe and needle disposal container ("disposal container") is disclosed. The disposal container comprises a plastic hinged case sized for encasing the majority of sizes of hypodermic syringes, with needles. Two securing tabs, opposite the hinge, secure the case in the closed position, thus securing the contents in the disposal container and preventing any contact with the secured contents by the handler. The disposal containers further includes a seal along its interior border for inhibiting fluids from leaking from the container. The disposal containers are retrieved by messengers for disposal in designated sites.

3 Claims, 3 Drawing Sheets

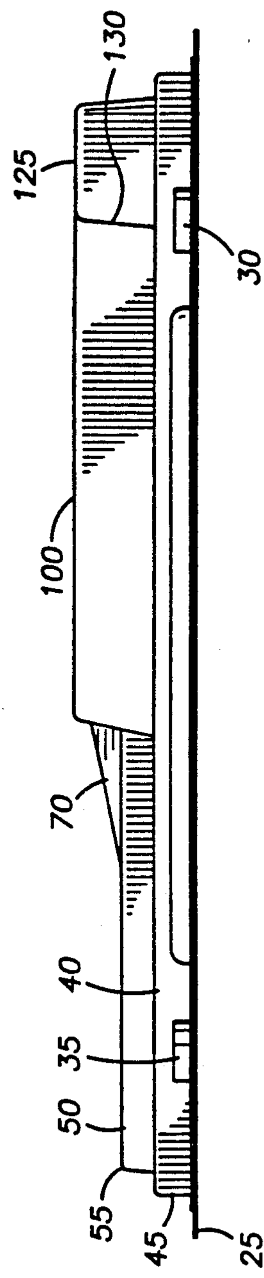
FIG. 3
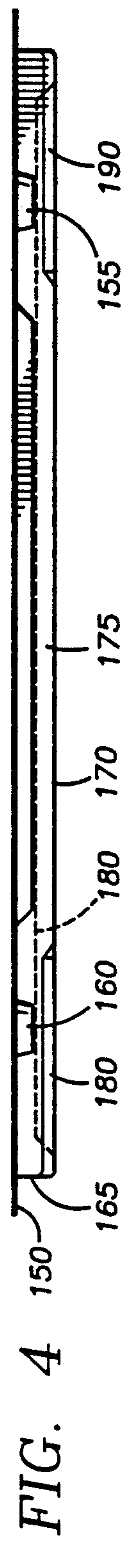
FIG. 4
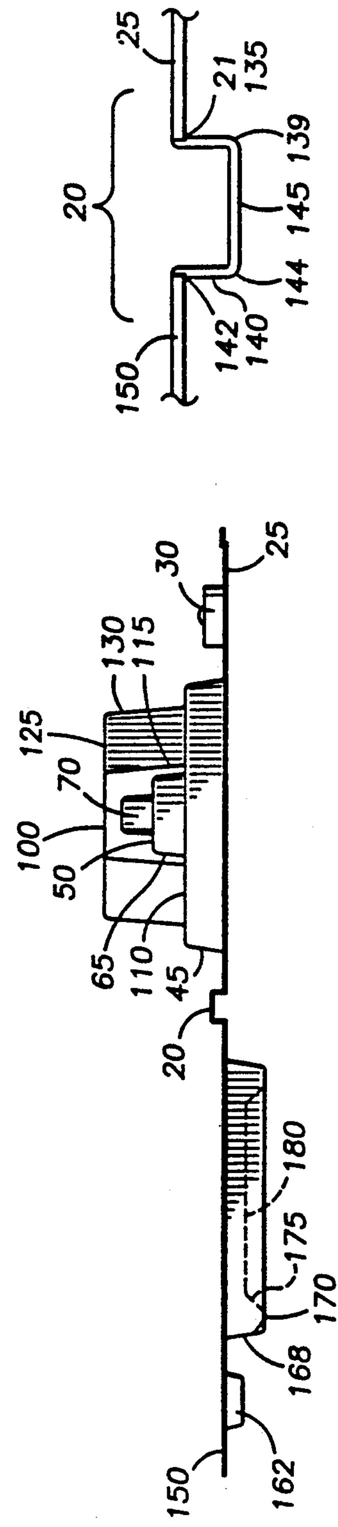
FIG. 6
FIG. 5

SYRINGE SEALING CONTAINER

FIELD OF THE INVENTION

The present invention relates to an apparatus and method for securing and disposing of hypodermic syringes with needles. More particularly, the present invention relates to an apparatus and method for encasing a hypodermic syringe, with needle, in a sealed environment which will reduce the possibility of contact by the handler with the secured contents.

BACKGROUND OF THE INVENTION

The present invention relates generally to the safe disposal of hypodermic syringes and needles. In the past, medical personnel and others, in the course of using and disposing of hypodermic syringes with needles, have suffered needle stick injuries which have presented serious health problems. Diseases such as hepatitis and AIDS may be transmitted by needle stick injuries. These diseases can lead to serious health problems, even the possibility of death. In recent years due to the increasing threat of AIDS, medical personnel who have contact with hypodermic syringes with needles must take increasing care to insure their safety.

An existing method used for protecting the handler from possible needle stick accidents from hypodermic syringes with needles is through the use of the protective sheath which is typically provided for covering the hypodermic syringe needle prior to the use of the syringe. With non-retractable syringes, the protective sheath could be used to recover the needle after use. Unfortunately, such use causes an inherent risk of a needle stick injury due to the possible careless or improper handling of the needle or sheath, especially reinstalling the sheath over the needle. Moreover, the United States Center for Disease Control guidelines now recommend against the recapping of syringes with the needle sheaths after use.

Another existing method used to minimize the risk of needle stick injuries is the use of a retractable syringe. A retractable syringe retracts and retains the possibly contaminated needle into the barrel of the syringe, and thus, protectively isolates the needle from further human contact. However, it is possible for some retractable syringes to leak contaminated fluids or residue through the opening where the needle is retracted into the syringe barrel. If excess contaminated fluids or residue leak, there is a risk of the contaminating virus or bacteria contaminating other medical tools or equipment in the area, and possibly infecting persons who subsequently come into contact with such tools, equipment, or the syringe. This existing risk of exposure to contaminated material gives rise to the need for further syringe and needle disposal protection.

Others have conceived and prepared models of the idea of a rigid, opaque, plastic case made up of identical sides to hold a single size hypodermic syringe and needle. The plastic case has a hinge, and there are multiple protuberances on one side to be received by openings on the other side.

It is an object of the present invention to provide a safe method of disposal for used hypodermic syringes with needles through use of a disposal container which is secured by tabs which are not easily reopened, securing the contents inside the disposal container.

It is another object of the present invention to provide a disposal container which will hold the majority of sizes of syringe and needle configurations available to medical and veterinary personnel.

It is another object of the present invention to provide a method of disposal of the hypodermic syringe and needle by including a well closure cover which will inhibit the leaking of contaminated fluids or residue which may happen to leak out of the syringe barrel or needle after use.

It is another object of the present invention to encase a hypodermic syringe and needle in such a fashion where it is unlikely that the syringe and/or needle may shift sufficiently to breach the disposal container in any manner, at any time during the transportation or disposal of the container and its contents.

SUMMARY OF THE INVENTION

The disposal container of the present invention comprises a molded set of pieces of flexible, transparent, plastic material including a syringe cavity base and a well closure cover which are connected by a hinge along the central vertical axis. The well closure cover contains two identical raised circular tabs across from the hinge. The syringe cavity base contains two identical circular receiver tabs, which are joined with the raised circular tabs to secure the disposal container in the closed position.

On the well closure cover, the plastic is molded in a raised elongated rectangular position with the center hollowed to approximately half the depth of the raised portion of the rectangle. An optional coating may be placed on the rectangular, built-up portion to provide a seal with the syringe cavity base when closed. The seal, once created between the well closure cover and the syringe cavity base, is extremely difficult to breach.

The syringe cavity base contains an indention which is slightly larger than the raised plastic portion on the well closure cover. The base and the cover fit tightly and securely together to form a seal around that portion of the container. The well closure cover is thus used to cover and secure the syringe cavity base, with the raised, hollowed surface serving as a safety container to inhibit or reduce the possibility of contaminated fluids or residue from leaking from the disposal container.

Along the central axis of the indented portion of the syringe cavity base, there is a further indention which serves to contain the syringe and needle. The bottom of the indention is sized to accommodate most sizes of syringe plungers and corresponding finger grips. The elongated portion of the indented cavity is sized to be wide and deep enough to accommodate most syringe barrels. At the top of the elongated cavity, an incline plane is located which angles up to a needle containing indention of the syringe cavity base. The incline plane allows for differing sizes of syringe and needle configurations to be housed in the container safely. The needle indention is shallow and is used to accommodate the needle portion of the syringe. The length of this indention is sized to be adequate for accommodating most medical and veterinary needles.

The disposal containers, in their sealed state, are collected by messenger service for disposal at proper sites.

BRIEF DESCRIPTION OF THE DRAWINGS

The accompanying drawings, which are incorporated in and constitute a part of the specification, in which like parts are given like reference referrals, illustrate preferred embodiments of the invention and, together with the general description of the invention given above and the detailed description of the preferred embodiments given below, serve to explain the principles of the invention.

FIG. 3: is a side view of the syringe cavity base, shown from the horizontal plane;

FIG. 4: is a side view of the well closure cover, shown from the horizontal plane;

FIG. 5: is a frontal view of the disposal container;

FIG. 6: is a cross section view of the hinge which connects the syringe cavity base and the well closure cover.

DESCRIPTION OF THE EMBODIMENTS

Structure

Figure 1:
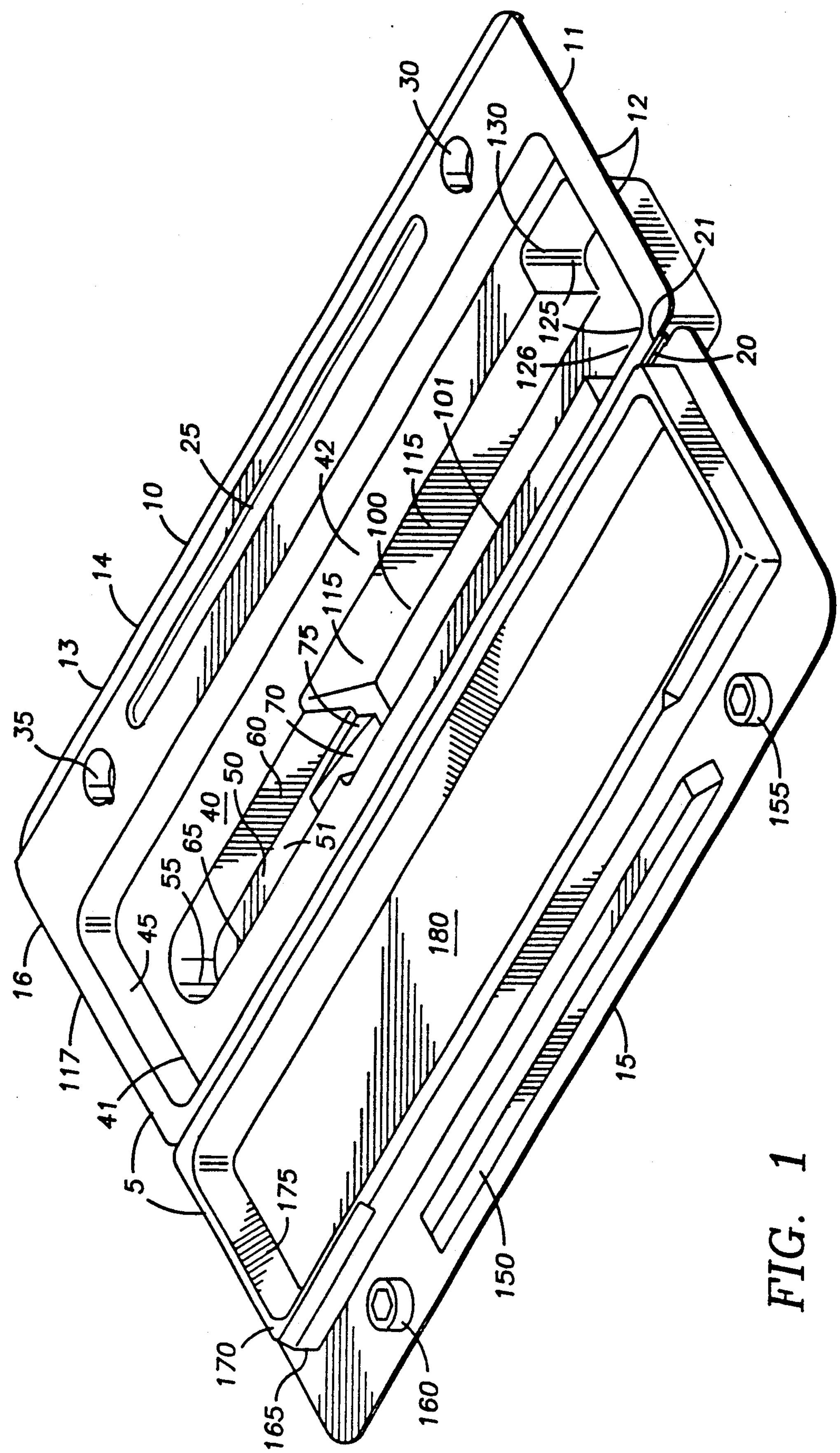
FIG. 1: is a profile view of the disposal container in the fully extended, open position.

The present invention discloses a hypodermic syringe disposal container. As shown in FIG. 1, the container 5 comprises a syringe cavity base 10 and a well closure cover 15. The base 10 and the cover 15 are connected by a continuous hinge 20.

The syringe cavity base 10 is typically 167 mm long and 61 mm wide. The syringe cavity base 10 includes a flat portion 25 with two depressed circular indentations 30, 35 set in from the end edge 11, 16 of base 12 and top 17, respectively, and the side edge 13 at side 14 of the syringe cavity base 10. Both indentations 30 and 35 are the same size typically with a diameter of 8 mm and a depth of 4 mm. Indentation 30 is typically located indented 23 mm from the end edge of base 12 of the syringe cavity base 10 and is typically located 8 mm set in from the side edge 13 of side 14 of the syringe cavity base 10. Indentation 35 is similarly located typically 23 mm indented from the opposing end edge 16 of top 17 of the syringe cavity base 10, and 8 mm from the side edge 13 of side 14 of the syringe cavity base 10.

The syringe cavity base 10 includes an elongated depressed indentation 27, which is centrally located between indentations 30 and 35 and is typically 85 mm long, 4 mm wide, and 3 mm deep.

The syringe cavity base 10 includes a depression 40 which is rectangular in shape with rounded corners. Depression 40 is typically located 7 mm from the end edge 11 of base 12 of syringe base 10, 18 mm from the side edge 13 of side 14 of syringe base 10, 7 mm from the top edge 16 of top 17 of syringe base 10, and 3 mm from the hinge edge 21 of hinge 20. Depression 40 is typically 38 mm wide and 150 mm long. Depression 40 is surrounded by walls 45 which are typically 6 mm deep. Depression 40 includes a floor 42, needle depression 50, barrel depression 100, and plunger depression 125. Needle depression 50 is centrally located inside of depression 40, typically 2 mm from the top edge 41 of the initial depression 40. Needle depression 50 is centrally located along the vertical axis of depression 40 and is typically 6 mm deeper than the floor 42 of depression 40. Needle depression 50 has a top edge 51 and extends for typically 60 mm along the floor 42. Needle depression 50 is walled at the top by a curved linear portion 55 and surrounded further by symmetrical walls 60, 65, all with a typical depth of 6 mm measured from the floor 42 of depression 40. An inclined plane 70 is formed in floor 42 starting from top edge 51. Inclined plane 70 is symmetrically located on the vertical central axis of needle depression 50. The inclined plane 70 is lined by walls 75 and 80 which are shaped as symmetrical elongated triangles. Typically inclined plane 70 begins 24 mm from the top edge 51 of depression 50 and angles downward. Inclined plane 70 is typically 15 mm long and 6 mm wide. The angle of inclination of inclined plane 70 is typically 15 degrees measured from the horizontal plane of needle depression 50.

Inclined plane 70 adjoins barrel depression wall 90. Wall 90 is curvilinear in the corners, and forms the top wall for barrel depression 100. Wall 90 is typically 16 mm wide. Cavity wall 90 extends from depression floor 51 to barrel depression floor 101. Barrel depression floor 101 is rectangular in shape and is surrounded by walls 90, 115, and 120. Barrel depression walls 115, 120, which are typically 16 mm deep measured from depression floor 42, are symmetric and typically extend 65 mm from barrel depression wall 90 to where they adjoin wall 130, which surrounds plunger depression floor 126.

Plunger depression floor 126 is typically 30 mm wide and 16 mm long, centered along the vertical axis. Plunger depression floor 126 is typically 12 mm deep measured from depression floor 42, and is surrounded by plunger depression wall 130, which is typically 12 mm high and curvilinear in all four corners. Plunger depression wall 130 is sloped outward towards depression floor 42.

Figure 2:
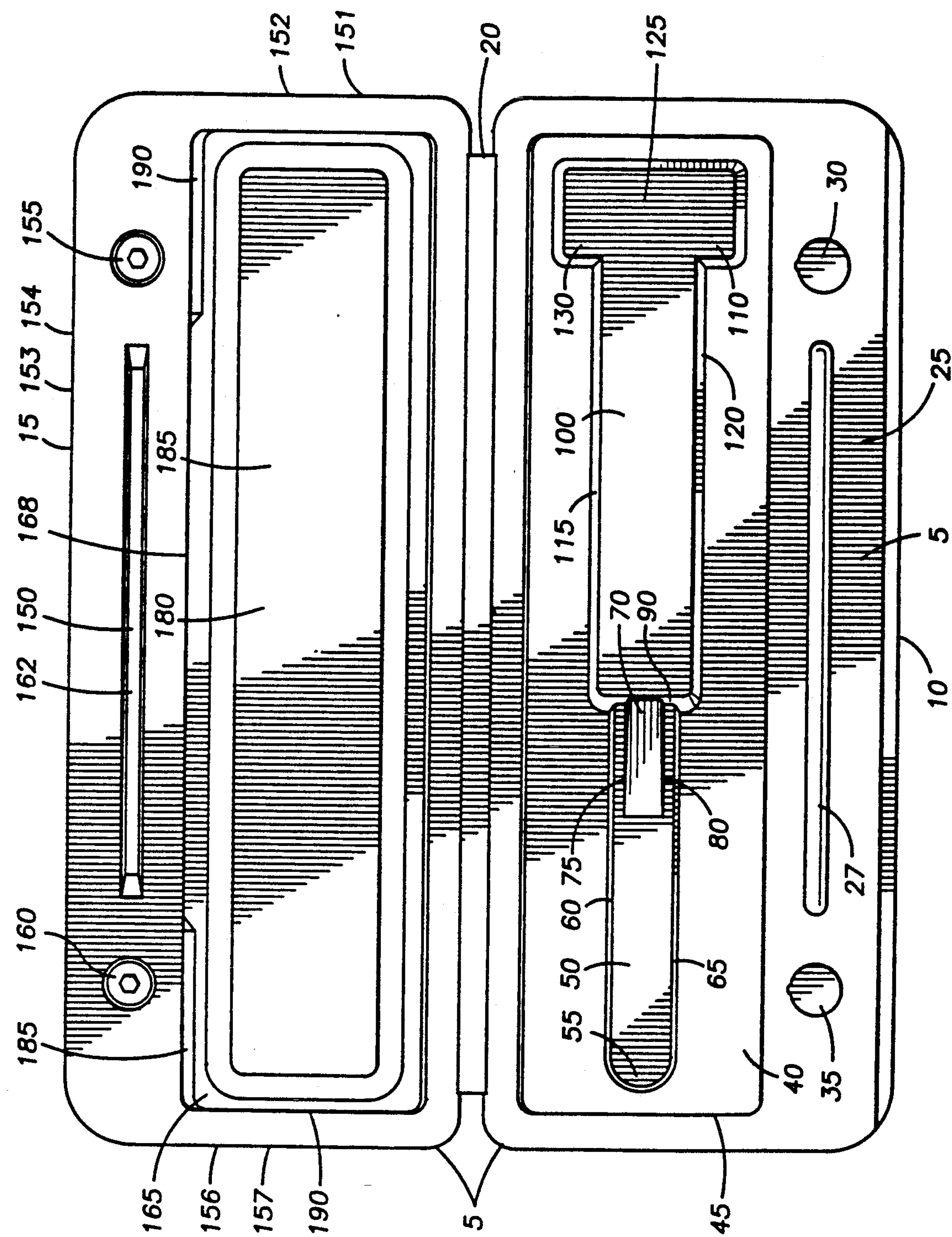
FIG. 2: is a top view of the open disposal container.

As shown in FIG. 2, which shows the syringe cavity base 10 on the left, raised towards the viewer, and the well closure cover 15 on the right, with the well cavity 162 depressed into the page, the well closure cover 15 comprises cover base 150 with two raised circular indentions 155 and 160. Well closure cover 15 includes end edges 151, 156 at base 152 and top edge 157, respectively, and side edge 154. The well closure cover 15 is typically 167 mm long and 62 mm wide. Both indentations 155 and 160 are the same size typically with a diameter of 7.5 mm and a depth of 3.5 mm. Indentation 155 is typically located 23 mm indented in from the end edge 151 of base 152 of the well closure cover 15 and is also typically indented 8 mm from the side edge 153 of side 154 of the well closure cover 15. Indentation 160 is similarly typically located 23 mm from the opposing end edge 156 of top edge 157 of well closure cover 15 and is also typically located 8 mm indented in from the side edge 153 of side 154 of the well closure cover 15.

The well closure cover 15 includes two protuberances 155, 160 and an elongated raised protuberance 162. Raise protuberance 162 is centrally located between protuberances 155, 160 and is typically 85 mm long, 4 mm wide, and 3 mm deep.

Cover base 150 of the well closure cover 15 extends inward to a built-up wall 165 which is rectangular in shape with rounded corners and is hollow in the center. Wall 165 is typically located 7 mm from the end edge 151 of base 152 of cover 15, 18 mm from the side edge 153 of side 154 of cover 15, 7 mm from the top edge 156 of top 157 of cover 15, and 3 mm from the hinge edge 142 of hinge 20. The height of wall 165 is typically 5 mm, width is 37 mm, and length is 149 mm. The wall top 170 adjoins wall 165 and is the same rectangular typically shape with a width of 2 mm extending towards the center of the rectangle. The hollow portion 185, in the center of the raised portion is formed by wall 175, with a typical depth of 2.5 mm, and by base 180. Wall 175 angles down to base 180 which is typically 25 mm wide and 137 mm long.

An optional sealant 190 may be placed on built-up wall 165, wall top 170, and as shown in FIG. 2, on a 2–5 mm boarder around the base of built-up wall 165 on base 150, where built-up wall 165 adjoins cover base 150 of well closure cover 15. The sealant 190 is a sticky substance which will adhere to the plastic material upon contact. When contact is made between the sealant and the plastic material, a seal is created which is difficult to breach.

Syringe cavity base 10 is connected to well closure cover 15 by hinge 20. FIG. 6 shows a cross-section of hinge 20, which includes two depressed hinge sides 135 and 140, which are typically 2 mm wide and 155 mm long. Hinge side 135 adjoins syringe cavity flat portion 25 at hinge edge 21 and adjoins hinge floor 140 at hinge edge 139. Similarly, hinge side 40 adjoins well closure cover flat portion 150 at hinge edge 142 and adjoins hinge floor 140 at hinge edge 144. Hinge floor 145 is typically 4 mm wide and 155 mm long. Hinge 20 is sufficiently elastic, due to the sizing of hinge sides 135, 140, and hinge floor 145, to allow the syringe cavity base 10 and the well closure cover 15 to remain in the open position, shown in FIG. 1, when the container 5 is held by only the syringe cavity base 10 or the well closure cover 15.

Manufacture

To achieve the foregoing object, and in accordance with the purposes of the invention as embodied and broadly described herein, methods available for producing such an object include vacuum forming, injection, or compression molding of a plastic material. The plastic materials available for such molding include polyvinyl chloride ("PVC"), polystyrene, polypropylene, acetate, polyethylene or any other thermo formed plastic. The material utilized should be capable of forming and folding with reasonable ease, and be capable of retaining its flexible character after manufacture. The material utilized should also be capable of remaining transparent subsequent to manufacture.

Method of Use

The hypodermic syringe and needle disposal container 5 is to be opened, and preferably started open, for each subsequent opening may cause the material to yield and make subsequent openings easier to achieve, to the position shown in FIG. 1 with the syringe cavity base 10 open to the top. The handler will place the hypodermic syringe and needle into the syringe cavity base 10 with the plunger fitting in to plunger depression 125, the syringe barrel in to barrel depression floor 100, the needle into needle depression 50, with the connection between the syringe and the needle resting upon the inclined plane 70. Upon placing the hypodermic syringe and needle into the disposal container, the handler will fold over the well closure cover 15 by securing the syringe cavity base 10 with one hand and folding the well closure cover 15 around the axis of rotation which runs through hinge 20. The well closure cover will be folded until the protuberances 154, 159 and outside wall 165 of the well closure cover 15 come in contact with the indentations 30, 35 and inside wall of the initial depression 45. The pieces are then pushed further together until the raised wall 165 of the well closure cover 15 is fully depressed into depression 40. If the sealant 190 is used, the last step will cause a tight seal to be formed between the well closure cover 15 and the syringe cavity base 10.

In order to further secure the well closure cove 15 to the syringe cavity base 10, the handler also forces protuberances 155, 160 into the depressed indentations 30, 35, respectively. The protuberances 155, 160 are to be inserted until base 150 becomes flush with base 25 and the elongated portions 27, 162 are fully inserted and flush.

When the disposal container is secure, the handler is then to lift the container and dispose of it in accordance with federal and state laws regarding the disposal of hazardous waste. The container should be handled with due diligence and care.

The embodiments set forth herein are merely illustrative and do not limit the scope of the invention or the details therein. It will be appreciated that many other modifications and improvements to the disclosure herein may be made without departing from the scope of the invention or the inventive concepts herein disclosed. Because many varying and different embodiments may be made within the scope of the inventive concept herein taught, including equivalent structures or materials hereafter thought of, and because many modifications may be more in the embodiments herein detailed in accordance with the descriptive requirements of the law, it is to be understood that the details herein are to be interpreted as illustrative and not in a limiting sense.

We claim:

1. A hypodermic syringe and needle disposal container for encasing a hypodermic syringe having a needle, a syringe body and a manipulation portion, comprising:
   - a syringe base having a cavity including containing means for receiving the hypodermic syringe;
   - a closure cover having a well and enclosing means for closing said containing means;
   - a hinge connected to said closure cover and said syringe base; and
   - a sealant on said closure cover having securing means for creating and maintaining a tight seal between said closure cover and said syringe base;;

wherein
   - said closure cover includes
     - a cover base;
     - a built-up portion;
   - said syringe base includes
     - an indented portion;
     - said built-up portion has an outer wall and a top surface sized to form a fluid flow inhibitor between said built-up portion and said indented portion; and
     - said sealant being placed on said cover base.

2. A hypodermic syringe and needle disposal container for encasing a hypodermic syringe having a needle, a syringe body and a manipulation portion, comprising:
   - a syringe base having a cavity including containing means for receiving the hypodermic syringe;
   - a closure cover having a well and enclosing means for closing said containing means;
   - a hinge connected to said closure cover and said syringe base; and
   - a sealant on said closure cover having securing means for creating and maintaining a tight seal between said closure cover and said syringe base;

wherein
   - said closure cover includes
     - a cover base;
     - a built-up portion;
   - said syringe base includes
     - an indented portion;

said built-up portion has an outer wall and a top surface sized to form a fluid flow inhibitor between said built-up portion and said indented portion; and said sealant being placed on said outer wall.

3. A hypodermic syringe and needle disposal container for encasing a hypodermic syringe having a needle, a syringe body and a manipulation portion, comprising:

a syringe base having a cavity including containing means for receiving the hypodermic syringe;

a closure cover having a well and enclosing means for closing said containing means;

a hinge connected to said closure cover and said syringe base; and a sealant on said closure cover having securing means for creating and maintaining a tight seal between said closure cover and said syringe base;

wherein said closure cover includes a cover base;

a built-up portion;

said syringe base includes an indented portion;

said built-up portion has an outer wall and a top surface sized to form a fluid flow inhibitor between said built-up portion and said indented portion; and said sealant being placed on said top surface.

* * * * *